(12) United States Patent
Page (10) Patent No.: US 12,022,895 B1
(45) Date of Patent: Jul. 2, 2024

(54) HEATED GLOVE

(71) Applicant: Tokoa Page, Rock Hill, SC (US)

(72) Inventor: Tokoa Page, Rock Hill, SC (US)

(*) Notice: Subject to any disclaimer, the term of this patent is extended or adjusted under 35 U.S.C. 154(b) by 882 days.

(21) Appl. No.: 17/074,742

(22) Filed: Oct. 20, 2020

(51) Int. Cl.
| | |
|---|---|
| *A61F 7/00* | (2006.01) |
| *A41D 1/00* | (2018.01) |
| *A41D 13/005* | (2006.01) |
| *A41D 19/00* | (2006.01) |
| *A41D 19/015* | (2006.01) |
| *H05B 3/00* | (2006.01) |

(52) U.S. Cl.
CPC ......... *A41D 13/0051* (2013.01); *A41D 1/002* (2013.01); *A41D 19/0024* (2013.01); *A41D 19/01535* (2013.01); *H05B 3/0019* (2013.01); *A61F 2007/0036* (2013.01); *H05B 2203/036* (2013.01)

(58) Field of Classification Search
CPC ............... A41D 13/0051; A41D 1/002; A41D 19/0024; A41D 19/01535; H05B 3/0019; H05B 2203/036; A61F 2007/0036
See application file for complete search history.

(56) References Cited

U.S. PATENT DOCUMENTS

| | | | |
|---|---|---|---|
| 3,710,075 A | * 1/1973 | Jablonowski | H05B 3/342 607/108 |
| 6,239,410 B1 | 5/2001 | Tackore | |
| D445,995 S | 8/2001 | Stanley | |
| 7,307,242 B1 | 12/2007 | Chen | |
| 8,664,571 B2 | 3/2014 | Macher | |
| 2008/0223844 A1 | 9/2008 | Cronn | |
| 2008/0229476 A1 | 9/2008 | Sanders | |
| 2009/0056107 A1 | 3/2009 | Williams | |
| 2011/0088138 A1 | 7/2011 | Hengami | |
| 2012/0074128 A1 | * 3/2012 | Blackford | A41D 13/0051 219/486 |
| 2014/0158673 A1 | 6/2014 | Gou | |
| 2015/0083704 A1 | 3/2015 | Guidry | |

FOREIGN PATENT DOCUMENTS

FR        3008283        1/2016

* cited by examiner

*Primary Examiner* — Tigist S Demie
(74) *Attorney, Agent, or Firm* — Kyle A. Fletcher, Esq.

(57) ABSTRACT

The heated glove is a garment. The heated glove comprises a glove and a control circuit. The control circuit mounts in the glove. The glove is worn on the hand of the client. The control circuit controls the temperature within the protected space provided by the glove. The control circuit is an electric circuit. The control circuit converts chemical potential energy into electrical energy used to heat the protected space provided by the glove.

14 Claims, 6 Drawing Sheets

HEATED GLOVE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including heating and cooling devices for medical or therapeutic treatment, more specifically, an electrically powered heating appliance. (A61F7/007)

Background Information

The anatomy of the human hand 200 is best understood by understanding the bones within the hand 200. The wrist 260 comprises 8 carpal bones that attach the fingers to the radius bone 261 and ulna bone 262 of the arm. Each finger is attached to the wrist 260 with a metacarpal bone. The thumb attaches to the wrist 260 with the proximal end of the first metacarpal 201 bone. The index finger attaches to the wrist 260 with the proximal end of the second metacarpal 202 bone. The middle finger attaches to the wrist 260 with the proximal end of the third metacarpal 203 bone. The ring finger attaches to the wrist 260 with the proximal end of the fourth metacarpal 204 bone. The little finger attaches to the wrist 260 with the proximal end of the fifth metacarpal 205 bone.

The thumb (First Finger 251) further comprises a first proximal phalange 211 and a first distal phalange 231. The bone structure of the thumb is completed by attaching the proximal end of the first proximal phalange 211 to the distal end of the first metacarpal 201 and attaching the proximal end of the first distal phalange 231 to the distal end of the first proximal phalange 211.

The index finger (Second Finger 252) further comprises a second proximal phalange 212, a second intermediate phalange 222, and a second distal phalange 232. The bone structure of the thumb is completed by attaching: 1) the proximal end of the second proximal phalange 212 to the distal end of the second metacarpal 202; 2) the proximal end of the second intermediate phalange 222 to the distal end of the second proximal phalange 212; and, 3) the proximal end of the second distal phalange 232 to the distal end of the second intermediate phalange 222.

The middle finger (Third Finger 253) further comprises a third proximal phalange 213, a third intermediate phalange 223, and a third distal phalange 233. The bone structure of the thumb is completed by attaching: 1) the proximal end of the third proximal phalange 213 to the distal end of the third metacarpal 203; 2) the proximal end of the third intermediate phalange 223 to the distal end of the third proximal phalange 213; and, 3) the proximal end of the third distal phalange 233 to the distal end of the third intermediate phalange 223.

The ring finger (Fourth Finger 254) further comprises a fourth proximal phalange 214, a fourth intermediate phalange 224, and a fourth distal phalange 234. The bone structure of the thumb is completed by attaching: 1) the proximal end of the fourth proximal phalange 214 to the distal end of the fourth metacarpal 204; 2) the proximal end of the fourth intermediate phalange 224 to the distal end of the fourth proximal phalange 214; and, 3) the proximal end of the fourth distal phalange 234 to the distal end of the fourth intermediate phalange 224.

The little finger (Fifth Finger 255) further comprises a fifth proximal phalange 215, a fifth intermediate phalange 225, and a fifth distal phalange 235. The bone structure of the thumb is completed by attaching: 1) the proximal end of the fifth proximal phalange 215 to the distal end of the fifth metacarpal 205; 2) the proximal end of the fifth intermediate phalange 225 to the distal end of the fifth proximal phalange 215; and, 3) the proximal end of the fifth distal phalange 235 to the distal end of the fifth intermediate phalange 225.

The first metacarpal 201 through the fifth metacarpal 205 are enclosed by what is referred to as the palm of the hand 200.

The human hand 200 is a grasping structure. The human hand 200 of the left side of the body is a mirror image of the human hand 200 of the right side of the body. The orientation is used to define the palm side 131 of the hand 200. Specifically, the left hand 200 and the right hand 200 can only be overlaid on top of each other when the palm side 131 of the left hand 200 is touching the palm side 131 of the right hand 200. The side of the hand 200 opposite to the palm side 131 is referred to as the back side 132. The human hand 200 is further defined with a thumb (first finger 251), index finger (second finger 252), middle finger (third finger 253), ring finger (fourth finger 254), and a little finger (fifth finger 255).

Within this disclosure, when referring to the bones of a hand 200, this disclosure will refer to the end of the bone that is closest to the wrist 260 as the proximal end and the end of the bone that is furthest from the wrist 260 as the distal end. This is consistent with medical terminology. Further, this disclosure will identify specific locations on the hand 200 by referring to the bone of the hand 200 that is proximal to the location.

A glove is an item of apparel that covers a hand 200. The glove comprises a plurality of finger stalls 111 into which the fingers of the hand 200 are inserted. Each finger stall is attached to a trank 112. The trank 112 is the portion of the glove that covers the palm of the hand 200. The palm side 131 of the trank 112 is proximal to the palm side 131 of the hand 200. The back side 132 of the trank 112 is proximal to the back side 132 of the hand 200. Typically: 1) the thumb from the first proximal phalange 211 to the first distal phalange 231 is inserted into the first finger stall 161; 2) the index finger from the second proximal phalange 212 to the second distal phalange 232 is inserted into the second finger stall 162; 3) the middle finger from the third proximal phalange 213 to the third distal phalange 233 is inserted into the third finger stall 163; 4) the ring finger from the fourth proximal phalange to the fourth distal phalange 234 is inserted into the fourth finger stall 164; and, 5) the little finger from the fifth proximal phalange 215 to the fifth distal phalange 235 is inserted into the fifth finger stall 165. This disclosure will identify specific locations on a glove by referring to the bone of the hand 200 that is proximal to the location.

SUMMARY OF INVENTION

The heated glove is a garment. The heated glove comprises a glove and a control circuit. The control circuit mounts in the glove. The glove is worn on the hand of the client. The control circuit controls the temperature within the protected space provided by the glove. The control circuit is an electric circuit. The control circuit converts chemical potential energy into electrical energy used to heat the protected space provided by the glove.

These together with additional objects, features and advantages of the heated glove will be readily apparent to those of ordinary skill in the art upon reading the following detailed description of the presently preferred, but nonetheless illustrative, embodiments when taken in conjunction with the accompanying drawings.

In this respect, before explaining the current embodiments of the heated glove in detail, it is to be understood that the heated glove is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the heated glove.

It is therefore important that the claims be regarded as including such equivalent construction insofar as they do not depart from the spirit and scope of the heated glove. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
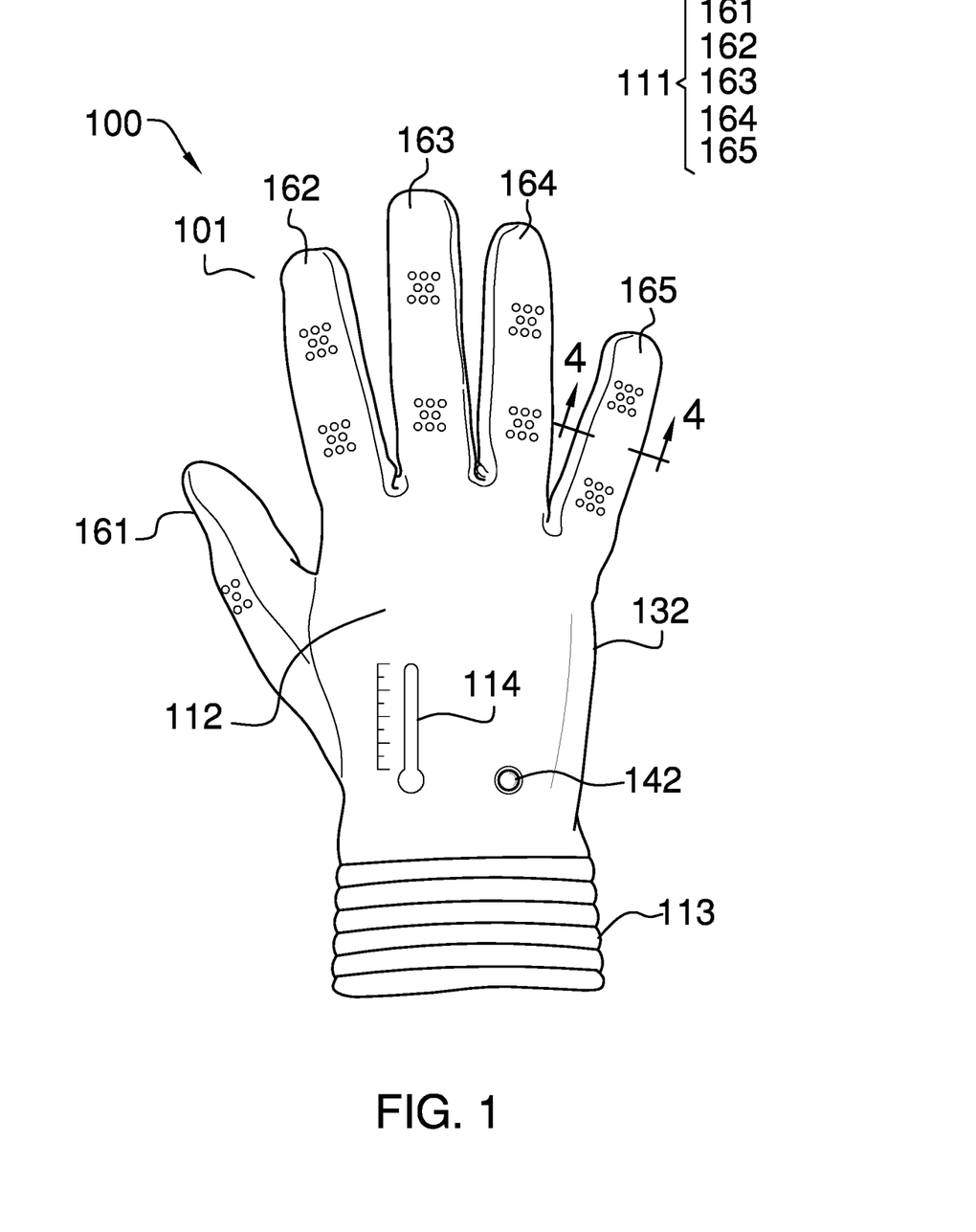
FIG. 1 is a back view of an embodiment of the disclosure.
Figure 2:
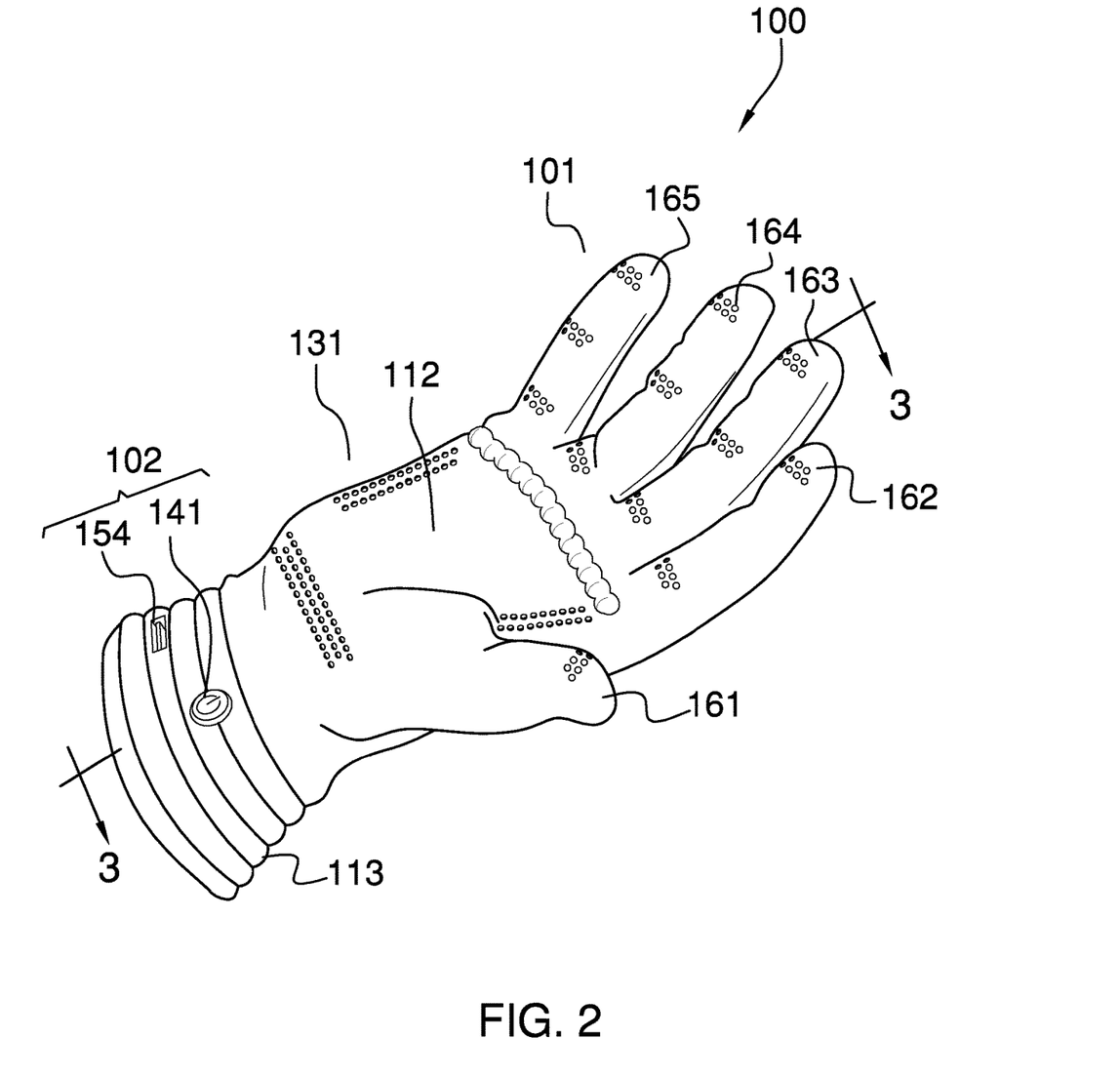
FIG. 2 is a perspective view of an embodiment of the disclosure.
Figure 3:
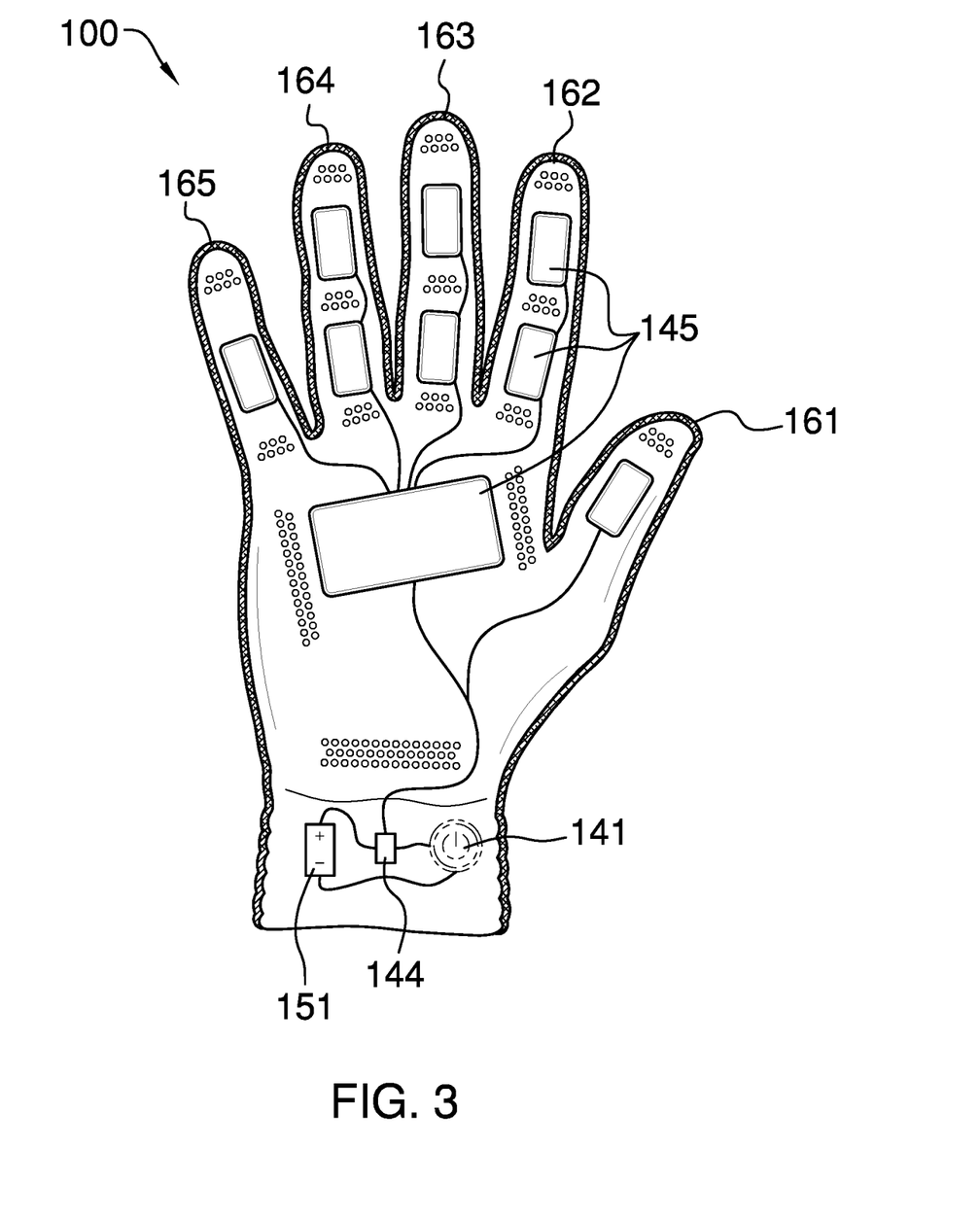
FIG. 3 is a cross-sectional view of an embodiment of the disclosure across 3-3 as shown in FIG. 2.
Figure 4:
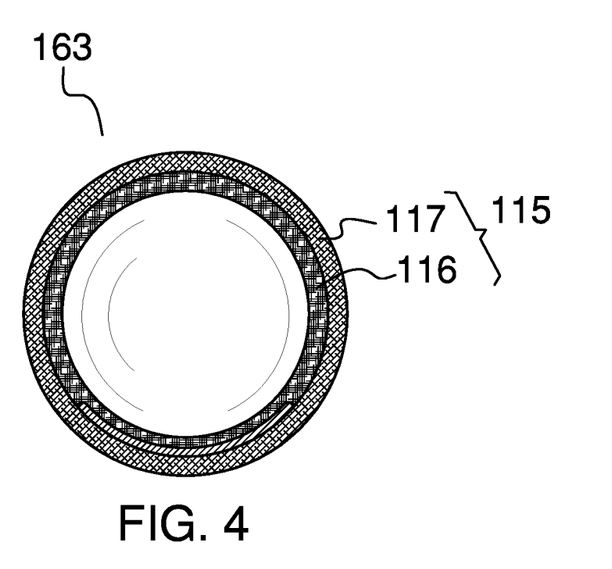
FIG. 4 is a cross-sectional view of an embodiment of the disclosure across 4-4 as shown in FIG. 1.
Figure 5:
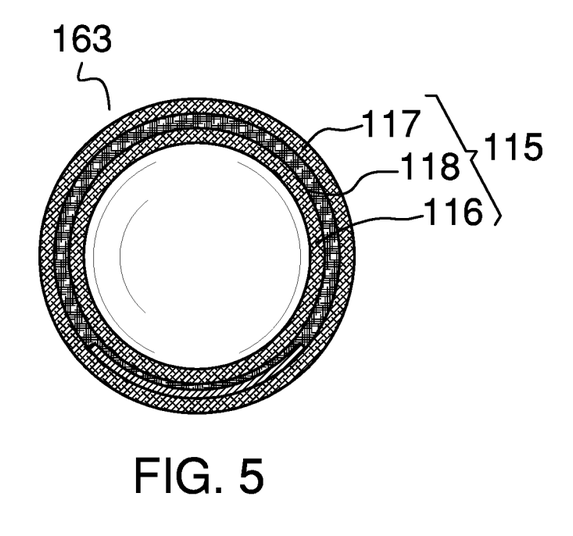
FIG. 5 is a cross-sectional view of an alternate embodiment of the disclosure across 4-4 as shown in FIG. 1.
Figure 6:
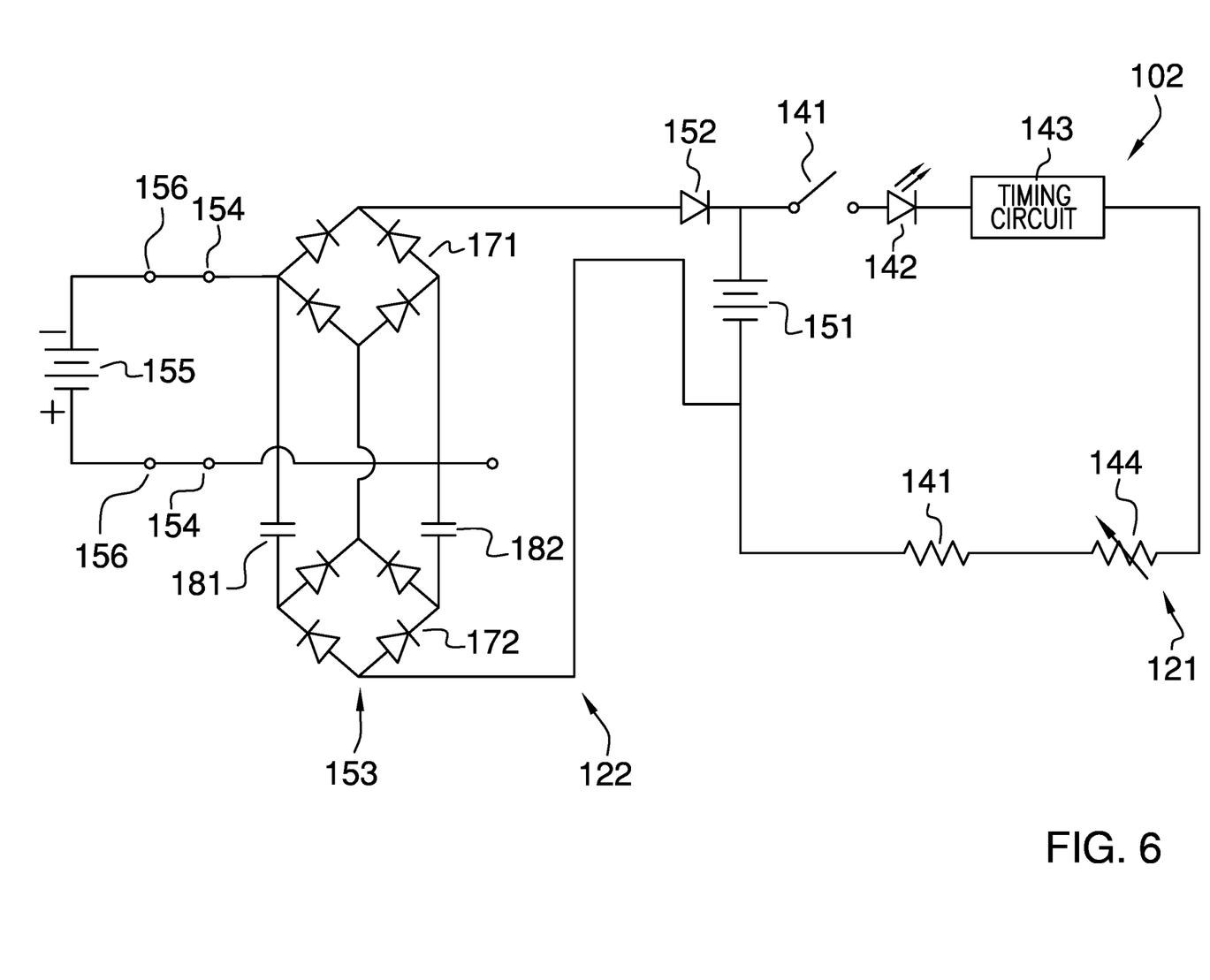
FIG. 6 is schematic view of an embodiment of the disclosure.
Figure 7:
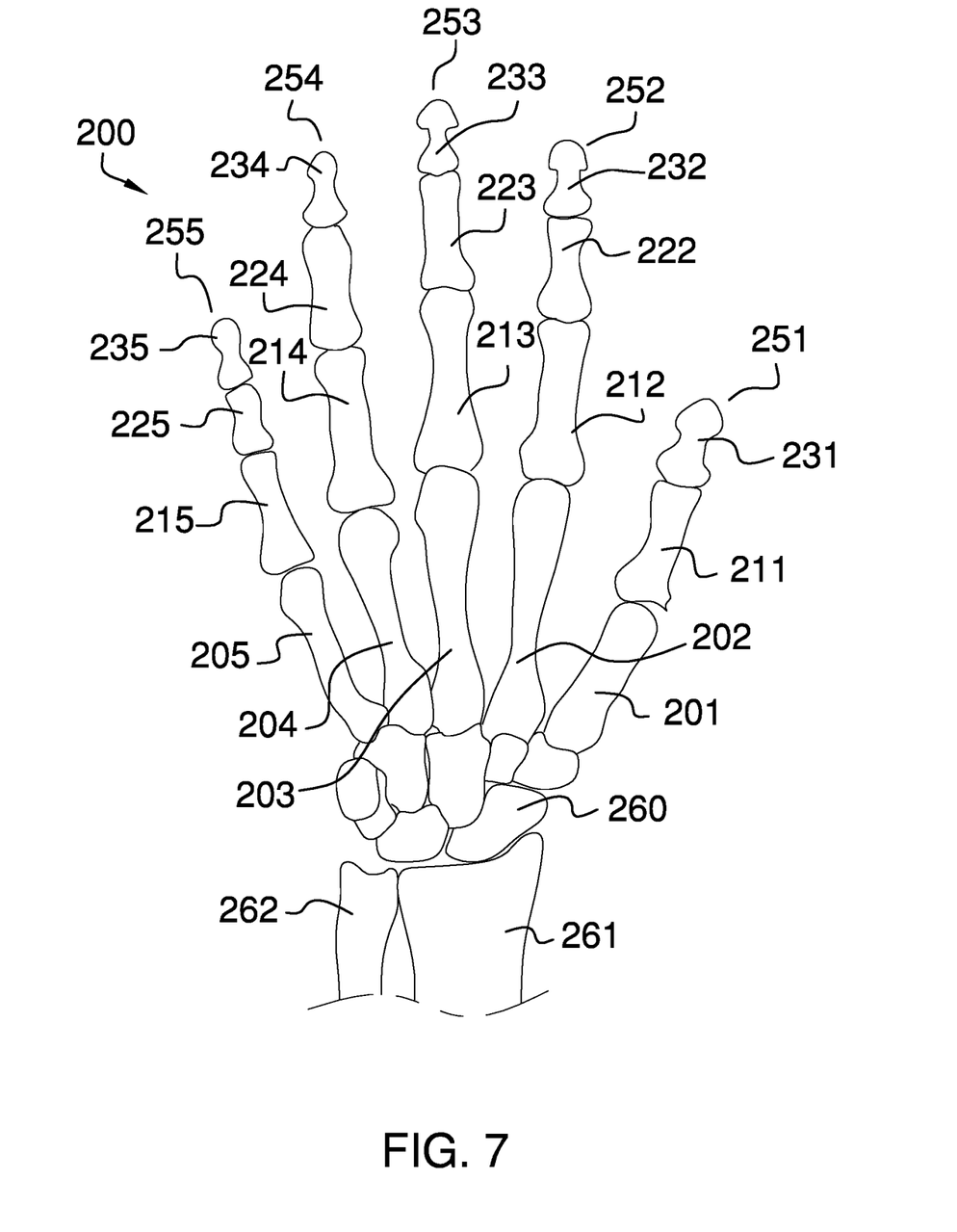
FIG. 7 is a detail view of an embodiment of the disclosure.

Detailed reference will now be made to one or more potential embodiments of the disclosure, which are illustrated in FIGS. 1 through 7.

19 The heated glove 100 (hereinafter invention) is a garment. The invention 100 comprises a glove 101 and a control circuit 102. The control circuit 102 mounts in the glove 101. The glove 101 is worn on the hand 200 of the client. The control circuit 102 controls the temperature within the protected space provided by the glove 101. The control circuit 102 is an electric circuit. The control circuit 102 converts chemical potential energy into electrical energy used to heat the protected space provided by the glove 101.

The glove 101 is a garment. The glove 101 is worn on the hand 200 of a client. The glove 101 forms a protected space that surrounds the hand 200. The glove 101 contains the control circuit 102. The glove 101 comprises a plurality of finger stalls 111, a trank 112, a wrist shell 113, and a temperature display 114.

Each of the plurality of finger stalls 111 is a finger stall. The finger stall is defined elsewhere in this disclosure. Each of the plurality of finger stalls 111 attaches to the trank 112 of the glove 101. Each of the plurality of finger stalls 111 is sized and positioned to receive a finger of the client. Each finger of the client enters its corresponding finger stall selected from the plurality of finger stalls 111 through the trank 112. The plurality of finger stalls 111 comprises a first finger stall 161, a second finger stall 162, a third finger stall 163, a fourth finger stall 164, and a fifth finger stall 165. The glove 101 further comprises a palm side 131 and a back side 132.

The first finger stall 161 is the stall selected from the plurality of finger stalls 111 that receives the first finger 251 of the client. The second finger stall 162 is the stall selected from the plurality of finger stalls 111 that receives the second finger 252 of the client. The third finger stall 163 is the stall selected from the plurality of finger stalls 111 that receives the third finger 253 of the client. The fourth finger stall 164 is the stall selected from the plurality of finger stalls 111 that receives the fourth finger 254 of the client. The fifth finger stall 165 is the stall selected from the plurality of finger stalls 111 that receives the fifth finger 255 of the client. The palm side 131 of the glove 101 is defined elsewhere in this disclosure. The back side 132 of the glove 101 is defined elsewhere in this disclosure.

The trank 112 is a sleeve structure that covers the palm of the hand 200. The plurality of finger stalls 111 and the wrist shell 113 attach to the trank 112. The trank 112 is formed with an opening that the hand 200 of the client inserts into. The trank 112 is defined elsewhere in this disclosure.

The wrist shell 113 is a sleeve that encloses the aperture formed in the trank 112. The wrist shell 113 encloses the wrist 260 of the client. In the first potential embodiment of the disclosure, the wrist shell 113 contains a portion of the control circuit 102.

The temperature display 114 is a temperature sensitive device. The temperature display 114 measures the temperature within the protected space formed by the glove 101. The temperature display 114 mounts on the glove 101 such that the temperature measured by the temperature display 114 is visible from the exterior side of the glove 101. The temperature display 114 mounts on the trank 112 of the glove 101 such that the temperature display 114 is visible from the back side 132 of the glove 101. In the first potential embodiment of the disclosure, the temperature display 114 is a temperature strip.

The glove 101 is formed from a base composite textile 115. The base composite textile 115 is a sheeting structure. The base composite textile 115 is formed as a composite textile structure. The base composite textile 115 forms the fabric that is used to assemble the glove 101. In the first potential embodiment of the disclosure, the base composite textile 115 comprises an inner layer 116 and an outer layer 117.

The inner layer 116 is the layer of the base composite textile 115 that is proximal to the hand of the client. The inner layer 116 is formed from an insulating material. The outer layer 117 is the layer of the base composite textile 115 that is distal to the hand of the client. The outer layer 117 is formed from an elastic material such that the outer layer 117 acts as a non-skid material that enhances the grip security of the client.

In a second potential embodiment of the disclosure, the base composite textile 115 further comprises a heat distribution foil 118. The heat distribution foil 118 is a layer of metal foil. The heat distribution foil 118 is sandwiched between the inner layer 116 and the outer layer 117. The heat distribution foil 118 forms a heat conductive structure that distributes the heat generated by the heating circuit 121 of the control circuit 102 through the protected space formed by the glove 101.

The control circuit 102 is an electric circuit. The control circuit 102 adjusts the temperature within the protected space formed by the glove 101. The control circuit 102 receives electrical energy from an external power source 155. The control circuit 102 converts the received electrical energy into chemical potential energy. The control circuit 102 converts the stored chemical potential energy back into electrical energy. The control circuit 102 uses the restored electrical energy generates heat that is used to adjust the temperature within the protected space formed by the glove 101. The control circuit 102 is an independently powered electric circuit. By independently powered is meant that the control circuit 102 can operate without an electrical connection to an external power source 155. The control circuit 102 comprises a heating circuit 121 and a power circuit 122. The heating circuit 121 and the power circuit 122 are electrically interconnected.

The heating circuit 121 is an electric circuit. The heating circuit 121 generates the heat used to warm the protected space formed by the glove 101. The heating circuit 121 comprises a master switch 141, an LED 142, a timing circuit 143, a potentiometer 144, and a heating element 145. The master switch 141, the LED 142, the timing circuit 143, the potentiometer 144, and the heating element 145 are electrically interconnected. The master switch 141, the LED 142, the timing circuit 143, the potentiometer 144, and the heating element 145 are electrically connected in a series circuit.

The master switch 141 forms the electrical connection between the power circuit 122 and the heating circuit 121. The master switch 141 controls the flow of electricity through the heating circuit 121. When the master switch 141 is in the closed position, the master switch 141 enables the operation of the heating circuit 121 by enabling the flow of electricity from the power circuit 122 into the heating circuit 121. When the master switch 141 is in the open position, the master switch 141 disables the operation of the heating circuit 121 by preventing the flow of electricity from the power circuit 122 into the heating circuit 121. The switch is defined elsewhere in this disclosure.

The LED 142 is a two terminal semiconducting device. The LED 142 generates an illumination when electricity flows through the LED 142. The LED 142 is illuminated when electric current is flowing through the heating element 145. The LED 142 mounts in the exterior surface of the back side 132 of the trank 112 such that the LED 142 is visible from the exterior of the glove 101. The LED 142 is defined elsewhere in this disclosure.

The timing circuit 143 is an electric circuit. The timing circuit 143 is a timing device. The timing circuit 143 controls the flow of electric energy through the heating circuit 121 in a cyclic manner. The timing circuit 143 permits the flow of electric energy through the heating circuit 121 for a first previously determined duration of time. The timing circuit 143 subsequently prevents the flow of electric energy through the heating circuit 121 for a second previously determined duration of time. At the end of the second previously determined duration of time, the timing circuit 143 restarts and again permits the flow of electric energy through the heating circuit for the first previously determined duration of time.

The heating element 145 is a resistive heating device. The flow of electric energy through the heating element 145 generates the heat used to warm the protected space formed by the glove 101. The amount of heat generated by the heating element 145 is a function of the amount of electric current flowing through the heating element 145.

The potentiometer 144 is an electric circuit element. The potentiometer 144 is a resistive circuit element. The potentiometer 144 is defined elsewhere in this disclosure. The potentiometer 144 is controlled by the client. The potentiometer 144 is wired in series with the heating element 145 such that the potentiometer 144 and the heating element 145 form a voltage divider. The voltage divider is defined elsewhere in this disclosure. The amount of electric current flowing through the heating element 145 is adjusted by adjusting the amount of resistance presented to the heating circuit 121 by the potentiometer 144.

The power circuit 122 is an electrical circuit. The power circuit 122 powers the operation of the control circuit 102. The power circuit 122 is an electrochemical device. The power circuit 122 converts chemical potential energy into the electrical energy required to power the control circuit 102. The power circuit 122 receives electrical energy from an external power source 155. The power circuit 122 converts the received electrical energy into chemical potential energy. The power circuit 122 converts the stored chemical potential energy back into electrical energy used to power the heating circuit 121. The power circuit 122 comprises a battery 151, a diode 152, a voltage doubling circuit 153, a charging port 154, and an external power source 155. The external power source 155 further comprises a charging plug 156. The battery 151, the diode 152, the voltage doubling circuit 153, the charging port 154, the external power source 155, and the charging plug 156 are electrically interconnected.

The battery 151 is an electrochemical device. The battery 151 converts chemical potential energy into the electrical energy used to power the control circuit 102. In the first potential embodiment of the disclosure, the battery 151 is a 9-volt battery 151.

The diode 152 is an electric circuit element. The diode 152 limits the flow of electricity through an electric circuit to a single direction. The diode 152 electrically connects between the battery 151 and the voltage doubling circuit 153 such that electric current will not flow from the positive terminal of the battery 151 into the voltage doubling circuit 153.

The voltage doubling circuit 153 is an electric circuit. The voltage doubling circuit 153 electrically connects between the charging port 154 and the battery 151/diode 152 combination. The voltage doubling circuit 153 receives an electrical voltage from the external power source 155 through the charging port 154. The voltage doubling circuit 153 presents double the electric voltage received from the external power source 155 to the battery 151. The voltage doubling circuit 153 does not increase the amount of energy transmitted from the external power source 155 into the battery 151. The voltage doubling circuit 153 further comprises a first bridge circuit 171, the second bridge circuit 172, the first capacitor 181, and the second capacitor 182. The first bridge circuit 171, the second bridge circuit 172, the first capacitor 181, and the second capacitor 182 are electrically interconnected.

The first bridge circuit 171 is a bridge circuit. The bridge circuit is defined elsewhere in this disclosure. The first bridge circuit 171 is formed from four diodes. The diode is defined elsewhere in this disclosure. The first bridge circuit 171 receives the full electrical voltage provided by the external power source 155. The first bridge circuit 171 is configured such that electric current entering the first bridge circuit 171 flows in a single direction. The second bridge circuit 172 is a bridge circuit. The second bridge circuit 172 is formed from four diodes. The diode is defined elsewhere in this disclosure. The second bridge circuit 172 receives the full electrical voltage provided by the external power source 155. The second bridge circuit 172 is configured such that electric current entering the second bridge circuit 172.

The first capacitor 181 is an electric circuit element. The capacitor is defined elsewhere in this disclosure. The first capacitor 181 electrically connects between the first bridge circuit 171 and the second bridge circuit 172. The purpose of the first capacitor 181 is to isolate the voltage across the first bridge circuit 171 from the voltage across the second bridge circuit 172. The second capacitor 182 is an electric circuit element. The capacitor is defined elsewhere in this disclosure. The second capacitor 182 electrically connects between the first bridge circuit 171 and the second bridge circuit 172. The purpose of the second capacitor 182 is to isolate the voltage across the first bridge circuit 171 from the voltage across the second bridge circuit 172.

This paragraph describes the theory of operation of the voltage doubling circuit 153. The first bridge circuit 171 and the second bridge circuit 172 are connected to the voltage presented by the external power source 155 as a parallel circuit. The first bridge circuit 171 and the second bridge circuit 172 are connected to each other as a series circuit. Because the flow of the electricity through the first bridge circuit 171 and the second bridge circuit 172 is limited to a single direction, the across the battery 151 equals the sum of the voltage across the first bridge circuit 171 and the voltage across the second bridge circuit 172. The first capacitor 181 and the second capacitor 182 isolate the first bridge circuit 171 from the second bridge circuit 172 by preventing the flow of electric current from the first bridge circuit 171 and the second bridge circuit 172 through the parallel circuit connections that are formed with the external power source 155. The use of the first capacitor 181 and the second capacitor 182 prevents potential dc electric current flows from equalizing the voltages across the first bridge circuit 171 and the second bridge circuit 172.

The charging port 154 is an electric port. The charging port 154 forms an electrical connection to the external power source 155 using the charging plug 156. The charging plug 156 removably inserts into the charging port 154 to form an electric connection between the voltage doubling circuit 153 and the external power source 155. The charging port 154 transfers the electric energy received from the external power source 155 to the voltage doubling circuit 153.

The external power source 155 is an externally provisioned source of electricity. In the first potential embodiment of the disclosure, the external power source 155 is a USB compatible voltage source. The external power source 155 transfers electric energy consistent with USB specifications to the voltage doubling circuit 153. The voltage doubling circuit 153 increases the voltage of the electric energy received from the external power source 155 before transferring it to the battery 151. By increasing the voltage relative to the external power source 155, the voltage doubling circuit 153 effectively doubles the storage capacity of the battery 151 for chemical potential energy.

The following definitions were used in this disclosure:

Appendage: As used in this disclosure, appendage is a generic term used to describe one or more limbs of a patient.

Barrier: As used in this disclosure, a barrier is a physical obstacle that forms a boundary between a first space and a second space. The barrier prevents the passage of an object between the first space and the second space.

Battery: As used in this disclosure, a battery is a chemical device consisting of one or more cells, in which chemical energy is converted into electricity and used as a source of power. Batteries are commonly defined with a positive terminal and a negative terminal.

Bridge Circuit: As used in this disclosure, a bridge circuit is an electrical circuit. The bridge circuit comprises four two terminal circuit elements that are electrically connected in a diamond pattern. By a diamond pattern is meant that a first series circuit and a second series circuit are electrically connected into a parallel circuit. In the bridge circuit, the first series circuit is formed by electrically connecting a first circuit element and a second circuit element in series. The second series circuit is formed by electrically connecting a third circuit element and a fourth circuit element in series. In an extension of version of a bridge circuit, a fifth two terminal circuit element is added to the bridge circuit with electrical connections made at: a) the electrical junction that connects the first circuit element and the second circuit element; and, b) the electrical junction that connects the third circuit element and the fourth circuit element. The extension of the bridge circuit is referred to in this disclosure as an "extended bridge circuit."

Capacitor: As used in this disclosure, a capacitor is an electrical device that is used to store an electric charge.

Client: As used in this disclosure, a client is an individual who is designated to receive the services of the disclosure at bar.

Composite Textile: As used in this disclosure, a composite textile is a multilayer fabric made of two or more joined layers of textile or sheeting materials.

Control Circuit: As used in this disclosure, a control circuit is an electrical circuit that manages and regulates the behavior or operation of a device.

Diode: As used in this disclosure, a diode is a two terminal semiconductor device that allows current flow in only one direction. The two terminals are called the anode and the cathode. Electric current is allowed to pass from the anode to the cathode.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Electric Circuit: As used in this disclosure, an electric circuit is a closed loop path through which electrons flow. The closed loop will generally initiate and terminate at an electrical power source.

External Power Source: As used in this disclosure, an external power source is a source of the energy that is externally provided to enable the operation of the present disclosure. Examples of external power sources include, but are not limited to, electrical power sources and compressed air sources.

Extremity: As used in this disclosure, extremity is a generic term used to describe either the hand and/or foot of a person. The extremity is located and the distal end of an appendage.

Finger Stall: As used in this disclosure, a finger stall refers to: 1) the roughly cylindrical structure associated with a glove into which a finger may be inserted; or, 2) a roughly cylindrical cover, commonly referred to as a finger cot, that is placed directly over a finger to cover the finger.

Foil: As used in this disclosure, a foil is a sheeting formed from a metal. Foils are flexible and are often used to cover a surface. A foil is also referred to as a metal leaf.

Garment: As used in this disclosure, a garment is a textile based structure that is used to cover an individual. Clothes, clothing, and apparel are synonyms for garment.

Glove: As used in this disclosure, a glove is an item of apparel that covers a hand. The glove comprises five finger stalls into which the fingers of the hand are inserted. The glove further comprises the trank which encloses the hand form the fingers to the wrist. A glove is further defined with a palm side and a back side. The palm side is proximal to the palm of the hand. The back side is distal from the palm side.

Hand: As used in this disclosure, the hand is the extremity of the arm. The hand attaches to the wrist at the end that is distal from the shoulder. The hand comprises a plurality of metacarpal bones and a plurality of phalange bones. Heating Element: As used in this disclosure, a heating element is a resistive wire that is used to convert electrical energy into heat. Common metal combinations used to form heat elements include a combination of nickel and Chromium (typical: 80/20), a combination of iron, chromium and aluminum (typical 70/25/5), a combination of copper, nickel, iron, and manganese (typical 66/30/2/2) (use for continuously hot), and platinum.

Interphalangeal Joint: As used in this disclosure, the interphalangeal joint refers to: 1) the joint that attaches a first selected phalange to a second selected phalange; or, 2) the joint that attaches a phalange to a metacarpal.

LED: As used in this disclosure, an LED is an acronym for a light emitting diode. A light emitting diode is a diode that is also a light source.

Maintained Switch: A used in this disclosure, a maintained switch is a switch that maintains the position that was set in the most recent switch actuation. A maintained switch works in an opposite manner to a momentary switch.

Metacarpal Bone: As used in this disclosure, the metacarpal bone refers to one of several bones of the hand that are enclosed by the palm of the hand.

Metal: As used in this disclosure, a metal is an element that readily loses electrons or an alloy formed from a plurality of such elements. General properties of metals include, but are not limited to, the ability to conduct heat, conduct electricity, malleability, and the ability to be drawn into a wire. For the purposes of this disclosure, the term metal is assumed to include the transition metals (columns 3-12 of the periodic table) and aluminum, tin, and lead. The alkali metals (columns 1 of the periodic table) and the alkali earth metals (column 2 of the periodic table) are assumed to be excluded from this definition.

Mirror Image: As used in this disclosure, a mirror image refers to a second object that is a reproduction of a first object wherein the second object is identical to the first object except that the orientation of the second object is reversed relative to the first object as if the second object has been reflected by a plane of a mirror (often called the mirror plane or plane of reflection).

Mitten: As used in this disclosure, a mitten is an item of apparel that covers a hand. The mitten comprises a single finger stall into which a thumb may be inserted. A mitten is further defined with a palm side and a back side. The palm side is proximal to the palm of the hand. The back side is distal from the palm side. See Finger Stall Non-Skid Material: As used in this disclosure, a non-skid material is a material or structure that can be applied to an object such that the object is inhibited from sliding along the surface upon which the object is resting. Non-skid materials are often, but not always, adhesive, elastic, or abrasive materials.

Palm: As used in this disclosure, the palm of the hand is identified as the portions of a left hand and a right hand between the fingers and the wrist that contact each other when the left hand presses against the right hand when the left hand and right hand are in alignment. The palm of the left hand is the mirror image of the palm of the right hand.

Parallel Circuit: As used in this disclosure, a parallel circuit refers to a method of electrically connecting a plurality of circuit elements to a voltage source. In a parallel circuit each circuit element receives a voltage equal to the full voltage produced by the voltage source.

Phalange Bone: As used in this disclosure, the phalange bone refers to one of several bones of the hand that are enclosed by the fingers of the hand.

Plug: As used in this disclosure, a plug is an electrical termination that electrically connects a first electrical circuit to a second electrical circuit or a source of electricity. As used in this disclosure, a plug will have two or three metal pins.

Port: As used in this disclosure, a port is an electrical termination that is used to connect a first electrical circuit to a second external electrical circuit. In this disclosure, the port is designed to receive a plug.

Potentiometer: As used in this disclosure, a potentiometer is an adjustable electrical device that presents a resistance to an electric. The level of resistance is adjustable.

Protected Space: As used in this disclosure, a protected space is a negative space within which an object is stored. The protected space is enclosed by a barrier structure that: a) prevents damage to the object contained within the protected space; or, b) maintains an environment suitable within the protected space that is appropriate for the object.

Purlicue: As used in this disclosure, the purlicue refers to the space between the thumb and the index finger of a hand.

Relaxed Shape: As used in this disclosure, a structure is considered to be in its relaxed state when no shear, strain, or torsional forces are being applied to the structure.

Resistance: As used in this disclosure, resistance refers to the opposition provided by an electrical circuit (or circuit element) to the electrical current created by a DC voltage is presented across the electrical circuit (or circuit element). The term impedance is often used for resistance when referring to an AC voltage that is presented across the electrical circuit (or circuit element).

Resistor: As used in this disclosure, a resistor is a well-known and commonly available electrical device that presents a resistance that inhibits the flow of electricity through an electric circuit. Within an electric circuit processing alternating currents, the resistor will not affect the phase of the alternating current. A current flowing through a resistor will create a voltage across the terminals of the resistor.

Sandwich: As used in this disclosure, to sandwich means to insert a first disk-shaped structure between a second disk-shaped structure and a third disk-shaped structure to form a composite prism structure. Specifically: a) a first congruent end of the first disk-shaped structure is placed against a first interior congruent end of the second disk-shaped structure; and, b) a second congruent end of the first disk-shaped structure is placed against a second interior congruent end of the third disk-shaped structure. A first exterior congruent end of the second disk-shaped structure forms a first overall congruent end of the overall composite prism structure described in this definition. A second exterior congruent end of the third disk-shaped structure forms a second overall congruent end of the overall composite prism structure described in this definition. The second overall congruent end of the overall composite prism structure is distal from the first overall congruent end. The verb to sandwich describes the act of placing the second disk-shaped structure between the first disk-shaped structure and the third disk-shaped structure.

Series Circuit: As used in this disclosure, a series circuit refers to a method of electrically connecting a plurality of circuit elements to a voltage source. In a series circuit, the proportion of the voltage received by each individual circuit element is divided proportionally between the plurality circuit elements based on the resistance (or impedance) of each circuit element relative to the total resistance of the plurality of circuit elements. The series circuit forms a linear or loop structure often referred to as a daisy chain.

Sheeting: As used in this disclosure, a sheeting is a material, such as a paper, textile, a plastic, or a metal foil, in the form of a thin flexible layer or layers. The sheeting forms a disk structure. The two surfaces of the sheeting with the greatest surface area are called the faces of the sheeting.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Temperature: As used in this disclosure, temperature refers to a relative measure of the kinetic and vibrational energy contained in the atoms and molecules of a first object (or system) relative to the kinetic and vibrational energy contained in the atoms and molecules of a second object (or system). When two objects (or systems) are in thermal equilibrium, the temperature of the two objects (or systems) is the same.

Temperature Strip: As use in this disclosure, a temperature strip is a mechanical device that physically changes its appearance as a function of temperature. The temperature strip is used to visibly display the temperature of the object it is attached to.

Textile: As used in this disclosure, a textile is a material that is woven, knitted, braided or felted. Synonyms in common usage for this definition include fabric and cloth. The two surfaces of the textile with the greatest surface area are called the faces of the textile.

Timing Circuit: As used in this disclosure, a timing circuit refers to an electrical network of interconnected electrical elements, potentially including but not limited to, resistors, capacitors, diodes, transistors, and integrated circuit devices. The purpose of the timing circuit is to generate an electrical control signal after a predetermined amount of time. In common usage, a timing circuit is also referred to as timing circuitry. The "555" timing circuit is a well-known, documented, and commercially available timing circuit.

Timing Device: As used in this disclosure, a timing device is an automatic mechanism for activating or deactivating a device at a specific time or after a specific period of time. This disclosure assumes that the logic module is provisioned with a timing circuit that can be used as a timing device. A timing device that activates an audible alarm is often referred to as a timer.

Trank: As used in this disclosure, the trank refers to the portion of a glove that covers the hand from the fingers to the wrist.

USB: As used in this disclosure, USB is an acronym for Universal Serial Bus which is an industry standard that defines the cables, the connectors, the communication protocols and the distribution of power required for interconnections between electronic devices. The USB standard defines several connectors including, but not limited to, USB-A, USB-B, mini-USB, and micro USB connectors. A USB cable refers to a cable that: 1) is terminated with USB connectors; and, 2) that meets the data transmission standards of the USB standard.

Volt: As used in this disclosure, a volt refers to the difference in electrical potential energy between two points in an electric circuit. A volt is measured as joules per coulomb. The term voltage refers to a quantitative measure of the volts between the two points.

Voltage Divider: As used in this disclosure, a voltage divider is an electric circuit that comprises a plurality of resistors electrically connected in series. The voltage divider divides a voltage presented across the plurality of resistors into one or more smaller voltages that can be used elsewhere in an electric circuit. The value of the one or more smaller voltages presented by the voltage divider is controlled through the selection of the value of each of the plurality of resistors.

Wrist: As used in this disclosure, the wrist refers to an eight bone structure within the human body that flexibly attaches the radial bone and the ulna bone to the metacarpal bones of the hand.

With respect to the above description, it is to be realized that the optimum dimensional relationship for the various components of the invention described above and in FIGS. 1 through 7 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A heated garment comprising
a glove and a control circuit;
wherein the glove contains the control circuit;
wherein the glove is worn on a hand of a client;
wherein the control circuit is an electric circuit;
wherein the control circuit controls a temperature within a protected space provided by the glove;
wherein the control circuit converts chemical potential energy into electrical energy used to heat the glove;
wherein the control circuit receives electrical energy from an external power source;
wherein the control circuit uses the restored electrical energy generates heat that is used to adjust the temperature within the protected space formed by the glove;
wherein the heating circuit comprises a master switch, an LED, a timing circuit, a potentiometer, and a heating element;
wherein the master switch, the LED, the timing circuit, the potentiometer, and the heating element are electrically interconnected;
wherein the glove is a garment;
wherein the glove is worn on the hand of a client;
wherein the control circuit converts chemical potential energy into electrical energy used to heat the protected space provided by the glove;
wherein the control circuit is an electric circuit;
wherein the control circuit adjusts the temperature within the protected space formed by the glove;
wherein the control circuit converts the received electrical energy into chemical potential energy;
wherein the control circuit converts the stored chemical potential energy back into electrical energy;
wherein the control circuit is an independently powered electric circuit;
wherein by independently powered is meant that the control circuit can operate without an electrical connection to an external power source;
wherein the glove comprises a plurality of finger stalls, a trank, a wrist shell, and a temperature display;
wherein the trank is a sleeve structure that covers the palm of the hand;
wherein the plurality of finger stalls and the wrist shell attach to the trank;
wherein the temperature display mounts on the glove;
wherein the trank is formed with an opening;
wherein the control circuit comprises a heating circuit and a power circuit;
wherein the heating circuit and the power circuit are electrically interconnected;
wherein the heating circuit is an electric circuit;
wherein the heating circuit generates the heat used to warm the protected space formed by the glove;
wherein the power circuit is an electrical circuit;
wherein the power circuit powers the operation of the control circuit;
wherein the power circuit is an electrochemical device;
wherein the power circuit converts chemical potential energy into the electrical energy required to power the control circuit;
wherein the power circuit receives electrical energy from the external power source;
wherein the power circuit converts the received electrical energy into chemical potential energy;
wherein the power circuit converts the stored chemical potential energy back into electrical energy used to power the heating circuit;
wherein the master switch, the LED, the timing circuit, the potentiometer, and the heating element are electrically connected in a series circuit.

2. The heated garment according to claim 1
wherein the power circuit comprises a battery, a power diode, a voltage doubling circuit, a charging port, and an external power source;
wherein the external power source further comprises a charging plug;
wherein the battery, the power diode, the voltage doubling circuit, the charging port, the external power source, and the charging plug are electrically interconnected.

3. The heated garment according to claim 2
wherein each of the plurality of finger stalls is a finger stall;
wherein each of the plurality of finger stalls attaches to the trank of the glove;
wherein each of the plurality of finger stalls is sized and positioned to receive a finger of the client;
wherein the wrist shell is a sleeve that encloses the aperture formed in the trank;
wherein the wrist shell encloses the wrist of the client;
wherein the wrist shell contains a portion of the control circuit.

4. The heated garment according to claim 3
wherein the plurality of finger stalls comprises a first finger stall, a second finger stall, a third finger stall, a fourth finger stall, and a fifth finger stall;
wherein the glove further comprises a palm side and a back side;
wherein the first finger stall is the stall selected from the plurality of finger stalls that receives the first finger of the client;
wherein the second finger stall is the stall selected from the plurality of finger stalls that receives the second finger of the client;
wherein the third finger stall is the stall selected from the plurality of finger stalls that receives the third finger of the client;
wherein the fourth finger stall is the stall selected from the plurality of finger stalls that receives the fourth finger of the client;
wherein the fifth finger stall is the stall selected from the plurality of finger stalls that receives the fifth finger of the client.

5. The heated garment according to claim 4
wherein the temperature display is a temperature sensitive device;
wherein the temperature display measures the temperature within the protected space formed by the glove;
wherein the temperature display mounts on the glove such that the temperature measured by the temperature display is visible from the exterior side of the glove;
wherein the temperature display mounts on the trank of the glove such that the temperature display is visible from the back side of the glove.

6. The heated garment according to claim 5
wherein the glove is formed from a base composite textile;
wherein the base composite textile is a sheeting structure;
wherein the base composite textile is formed as a composite textile structure;
wherein the base composite textile forms the fabric that is used to assemble the glove;
wherein the base composite textile comprises an inner layer and an outer layer;
wherein the inner layer is the layer of the base composite textile that is proximal to the hand of the client;
wherein the inner layer is formed from an insulating material;
wherein the outer layer is the layer of the base composite textile that is distal to the hand of the client;
wherein the outer layer is formed from an elastic material such that the outer layer acts as a non-skid material that enhances the grip security of the client.

7. The heated garment according to claim 6
wherein the base composite textile further comprises a heat distribution foil;
wherein the heat distribution foil is a layer of metal foil;
wherein the heat distribution foil is sandwiched between the inner layer and the outer layer;
wherein the heat distribution foil forms a heat conductive structure that distributes the heat generated by the heating circuit of the control circuit through the protected space formed by the glove.

8. The heated garment according to claim 7
wherein the master switch forms the electrical connection between the power circuit and the heating circuit;
wherein the master switch controls a flow of electricity through the heating circuit;
wherein when the master switch is in the closed position, the master switch enables the operation of the heating circuit by enabling the flow of electricity from the power circuit into the heating circuit;
wherein when the master switch is in the open position, the master switch disables the operation of the heating circuit by preventing the flow of electricity from the power circuit into the heating circuit.

9. The heated garment according to claim 8
wherein the LED is a two terminal semiconducting device;
wherein the LED generates an illumination when electricity flows through the LED;
wherein the LED is illuminated when electric current is flowing through the heating element;
wherein the LED mounts in the exterior surface of the back side of the trank such that the LED is visible from the exterior of the glove.

10. The heated garment according to claim 9
wherein the timing circuit is an electric circuit;
wherein the timing circuit is a timing device;
wherein the timing circuit controls the flow of electric energy through the heating circuit in a cyclic manner;
wherein the timing circuit permits the flow of electric energy through the heating circuit for a first previously determined duration of time;
wherein the timing circuit subsequently prevents the flow of electric energy through the heating circuit for a second previously determined duration of time;
wherein at the end of the second previously determined duration of time, the timing circuit restarts and again permits the flow of electric energy through the heating circuit for the first previously determined duration of time.

11. The heated garment according to claim 10
wherein the heating element is a resistive heating device;
wherein the flow of electric energy through the heating element generates the heat used to warm the protected space formed by the glove;
wherein the amount of heat generated by the heating element is a function of the amount of electric current flowing through the heating element;
wherein the potentiometer is an electric circuit element;
wherein the potentiometer is a resistive circuit element;
wherein the potentiometer is controlled by the client;
wherein the potentiometer is wired in series with the heating element such that the potentiometer and the heating element form a voltage divider;
wherein the amount of electric current flowing through the heating element is adjusted by adjusting the amount of resistance presented to the heating circuit by the potentiometer.

12. The heated garment according to claim 11
wherein the power diode is an electric circuit element;
wherein the power diode limits the flow of electricity through an electric circuit to a single direction;
wherein the power diode electrically connects between the battery and the voltage doubling circuit such that electric current will not flow from the battery into the voltage doubling circuit;
wherein the voltage doubling circuit is an electric circuit;
wherein the voltage doubling circuit electrically connects between the charging port and the battery/power diode combination;
wherein the voltage doubling circuit receives an electrical voltage from the external power source through the charging port;
wherein the voltage doubling circuit presents double the electric voltage received from the external power source to the battery;
wherein the charging port is an electric port;
wherein the charging port forms an electrical connection to the external power source using the charging plug;
wherein the charging plug removably inserts into the charging port to form an electric connection between the voltage doubling circuit and the external power source;
wherein the charging port transfers the electric energy received from the external power source to the voltage doubling circuit;
wherein the external power source is an externally provisioned source of electricity.

13. The heated garment according to claim 12
wherein the voltage doubling circuit further comprises a first bridge circuit, the second bridge circuit, the first capacitor, and the second capacitor;
wherein the first bridge circuit, the second bridge circuit, the first capacitor, and the second capacitor are electrically interconnected;
wherein the first bridge circuit is a bridge circuit;
wherein the first bridge circuit is formed from four diodes;
wherein the first bridge circuit receives the full electrical voltage provided by the external power source;
wherein the first bridge circuit is configured such that electric current entering the first bridge circuit flows in a single direction;
wherein the second bridge circuit is a bridge circuit;

wherein the second bridge circuit is formed from four diodes;

wherein the second bridge circuit receives the full electrical voltage provided by the external power source;

wherein the second bridge circuit is configured such that electric current entering the second bridge circuit;

wherein the first capacitor is an electric circuit element;

wherein the first capacitor electrically connects between the first bridge circuit and the second bridge circuit;

wherein the second capacitor is an electric circuit element;

wherein the second capacitor electrically connects between the first bridge circuit and the second bridge circuit.

14. The heated garment according to claim 13 wherein the temperature display is a temperature strip; wherein the battery is a 9-volt battery.

\* \* \* \* \*